United States Patent
Koshti et al.

(10) Patent No.: US 9,661,847 B2
(45) Date of Patent: May 30, 2017

(54) ANTIMICROBIAL PRESERVATIVE COMPOSITIONS FOR PERSONAL CARE PRODUCTS

(71) Applicant: Galaxy Surfactants Ltd., Maharashtra (IN)

(72) Inventors: Nirmal Koshti, Mumbai (IN); Shraddha Kiran Ratnaparkhe, Thane West (IN); Devyani Ashok Mali, Ambernath (IN); Bhagyesh Sawant, Kalyan (IN); Pooja Dinkar Vaidya, Maharashtra (IN)

(73) Assignee: Galaxy Surfactants Ltd., Maharashtra (IN)

( * ) Notice: Subject to any disclaimer, the term of this patent is extended or adjusted under 35 U.S.C. 154(b) by 141 days.

(21) Appl. No.: 14/357,663

(22) PCT Filed: Nov. 23, 2012

(86) PCT No.: PCT/IB2012/056674
§ 371 (c)(1),
(2) Date: May 13, 2014

(87) PCT Pub. No.: WO2013/076697
PCT Pub. Date: May 30, 2013

(65) Prior Publication Data
US 2014/0309302 A1    Oct. 16, 2014

(30) Foreign Application Priority Data
Nov. 25, 2011   (IN) .......................... 3026/MUM/2011

(51) Int. Cl.
| A61K 8/42 | (2006.01) |
| A61K 8/44 | (2006.01) |
| A61K 8/34 | (2006.01) |
| A01N 31/14 | (2006.01) |
| A01N 37/20 | (2006.01) |
| A01N 37/46 | (2006.01) |
| A01N 37/44 | (2006.01) |

(Continued)

(52) U.S. Cl.
CPC ............ *A01N 37/44* (2013.01); *A01N 31/14* (2013.01); *A01N 37/20* (2013.01); *A01N 37/46* (2013.01); *A61K 8/33* (2013.01); *A61K 8/34* (2013.01); *A61K 8/345* (2013.01); *A61K 8/42* (2013.01); *A61K 8/44* (2013.01); *A61Q 5/02* (2013.01); *A61Q 17/005* (2013.01); *A61Q 17/04* (2013.01); *A61Q 19/00* (2013.01); *A61Q 19/10* (2013.01); *A61K 2800/5922* (2013.01); *A61Q 9/02* (2013.01)

(58) Field of Classification Search
CPC . A61K 8/347; A61K 8/42; A61K 8/44; A01N 37/18; A01N 31/14; A01N 37/20; A01N 37/46; A61Q 17/00
See application file for complete search history.

(56) References Cited

U.S. PATENT DOCUMENTS 3,193,451 A   7/1965  Reinisch
3,385,755 A   5/1968  Seebohm
(Continued)

FOREIGN PATENT DOCUMENTS

| EP | 0747047 B1 | 7/1998 |
| EP | 0983055 B1 | 4/2004 |
| GB | 2354771 A | 4/2001 |
| HU | 9800933 A2 | 3/2001 |
| WO | 9927902 A1 | 6/1999 |
| WO | 2007104879 A2 | 9/2007 |

OTHER PUBLICATIONS

Kang et al., Decreased Sperm Number and Motile Activity on the F1 Offspring Maternally Exposed to Butyl p-Hydroxybenzoic Acid (Butyl Paraben), J. Vet. Med. Sci., 2002, pp. 227-235, vol. 64, No. 3.

(Continued)

*Primary Examiner* — Irina Neagu
(74) *Attorney, Agent, or Firm* — The Webb Law Firm

(57) ABSTRACT

A personal product antimicrobial preservative composition for preservation of topical personal care formulations is provided and includes [A] one or more undecylenic acid derivatives depicted by Formula (I), Formula I

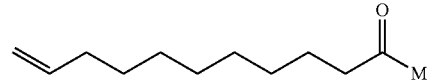

[B] one or more octanoic acid derivatives depicted by Formula (II),

Formula (II)

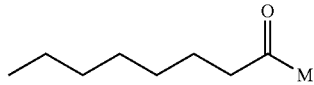

and [C] 2-phenoxy ethanol or 2-ethyl hexyl glyceryl ether or mixture of these two 'liquid alcohol ethers'; wherein, each of the two components [A] and [B] is present in the range of 5 to 20% by weight and together [A] and [B] constitute 10 to 30% by weight and the 'liquid alcohol ether', component [C], is present 70 to 90% by weight of the total preservative composition. A method for preserving personal care product from microbial attack is provided containing an aqueous phase comprising three component composition from about 0.5 to 2.5% by weight of the total personal care formulation.

9 Claims, No Drawings

(51) Int. Cl.

| | |
|---|---|
| *A61K 8/33* | (2006.01) |
| *A61Q 5/02* | (2006.01) |
| *A61Q 17/00* | (2006.01) |
| *A61Q 17/04* | (2006.01) |
| *A61Q 19/00* | (2006.01) |
| *A61Q 19/10* | (2006.01) |
| *A61Q 9/02* | (2006.01) |

(56) References Cited

U.S. PATENT DOCUMENTS

| | | | |
|---|---|---|---|
| 3,883,661 A * | 5/1975 | Young | 514/625 |
| 5,736,574 A | 4/1998 | Burnier et al. | |
| 2002/0058010 A1 | 5/2002 | Picard-Lesboueyries et al. | |
| 2003/0215409 A1* | 11/2003 | Quinn et al. | 424/70.1 |
| 2004/0096528 A1 | 5/2004 | Miser et al. | |
| 2004/0241261 A1* | 12/2004 | Prous et al. | 424/776 |
| 2004/0265263 A1 | 12/2004 | McDonald et al. | |
| 2008/0226568 A1 | 9/2008 | Rozsa et al. | |

OTHER PUBLICATIONS

Preservatives for Personal Care, Apr. 2012, 6 pages, Ashland, Covington, KY.

Steinberg, David, Combinations and Solutions, Preservatives for Cosmetics, 2006, pp. 78-79, Chapter 4.

Ash et al., "Handbook of Preservatives", 2004, pp. 365 and 1067, Synapse Information Resources, Inc., Endicott, NY.

D'Alelio et al., "A Series of N-Methyl Amides", Journal of the American Chemical Society, Jan. 1937, pp. 109-111, vol. 59:1.

D'Alelio et al., "Three Series of N-Substituted Aliphatic Amides", Journal of the American Chemical Society, Jan. 1937, pp. 111-112, vol. 59:1.

Harvey et al., "Endocrine Disrupters and Human Health: Could Oestrogenic Chemicals in Body Care Cosmetics Adversely Affect Breast Cancer Incidence in Women?" Journal of Applied Toxicology, 2004, pp. 167-176, vol. 24.

Kabara (Ed.), "Cosmetic and Drug Preservation: Principles and Practice", 1984, pp. 84-85, vol. 1, Marcel Dekker, Inc., New York, New York.

"New cosmetic formulations", Research Disclosure, Mar. 2001, vol. 443:43.

Orth, "Standardizing Preservative Efficacy Test Data", Cosmetics & Toiletries, Mar. 1991, pp. 45-51, vol. 106.

Pedersen et al., "The Preservatives Ethyl-, Propyl-, and Butylparaben are Oestrogenic in an in vivo Fish Assay", Pharmacology & Toxicology, 2000, pp. 110-113, vol. 86.

Woodruff, "Getting the balance right", Soap, Perfumery & Cosmetics, Sep. 2006, pp. 51-54.

* cited by examiner

ANTIMICROBIAL PRESERVATIVE COMPOSITIONS FOR PERSONAL CARE PRODUCTS

CROSS-REFERENCE TO RELATED APPLICATIONS

This application is the United States national phase of International Application No. PCT/IB2012/056674 filed Nov. 23, 2012, and claims priority to Indian Patent Application No. 3026/MUM/2011 filed Nov. 25, 2011, the disclosures of which are hereby incorporated in their entirety by reference.

FIELD OF THE INVENTION

The present invention relates to the preservation of personal care formulations with synergistic blends of three types of ingredients that offer a broad spectrum of activity against the microbes namely, an undecylenic acid derivative of Formula (I), an octanoic acid component of Formula (II) and a liquid alcohol ether, 2-phenoxy ethanol or 2-ethyl hexyl glyceryl ether or blend of the two. Further, the invention relates to the use of the combinations of three types of cosmetic ingredients.

BACKGROUND AND PRIOR ART OF THE INVENTION

Preservation of personal care products from microbial contamination has become a difficult task since the available approved antimicrobials are very few and those which have good antimicrobial activity are quite toxic. Consumers want products meant for topical applications to be free from toxic antimicrobials that are used as preservatives. This situation is partly addressed by exploiting the synergy between disparate of antimicrobials. It allows one to achieve not only the broad spectrum of activity against the variety of microbes but high level of antimicrobial efficacy is achieved despite reducing the concentration of individual antimicrobial. Commercially, such synergistic blends are available where antifungal chemicals are combined with antibacterial chemicals.

Currently, a number of blends are available for preservation of personal care products where synergy between antimicrobials is exploited in lowering the concentration of individual ingredient and another great advantage is that the microbes cannot develop resistance very easily if they are attacked by a combination of antimicrobials.

The following are the leading manufacturers of antimicrobials that offer synergistic blends to tackle the preservation of personal care products. BASF/Cognis (Germany), Thor (England), Schulke and Mayr (Germany), International Specialty Products (ISP, USA), Rohm and Haas (USA), Lonza (Germany/Switzerland), Arch Personal Care Products (USA), Nalco (USA) Rhodia-McIntyre (France-USA), Clamant (Germany), Induchem (Switzerland), and Symrise (USA), Sharon Laboratories (Israel) and Galaxy Surfactants Ltd (India).

The most effective antimicrobials that are used for creating these combinations for topical personal care products can be classified into four major categories. The four categories are 1) phenolic antimicrobials 2) formaldehyde releasing compounds 3) quaternary ammonium compounds and 4) halogenated antimicrobials. The examples of phenolic compounds are parabens and the examples of phenolic halogenated compounds are, Triclosan and chloroxylenol. Chloroxylenol is significantly toxic to mammals and is a skin irritant with quite allergic properties. The examples of nonphenolic halogenated compounds are 2-bromo-2-nitro-1,3 propane diol, and chloroisothiazolinone. The examples of formaldehyde releasing compounds are DMDM hydantoin, diimidazolidinyl urea and examples of quaternary ammonium compounds are benzethonium chloride and cetyl pyridinium chloride.

Parabens:

Parabens are esters of p-hydroxy benzoic acid. Some parabens are active against bacteria and some show activity against fungi. Usually they are used in combination of at least two or in most cases combination of 4 to 5. In fact all five (methyl, ethyl, propyl, butyl and isobutyl) parabens are often times combined with other antimicrobial to seek lower dosage and synergy in the antimicrobial efficacy. For example, Clariant's 'Phenonip' is a blend of six antimicrobials out of which the five are parabens. The same company offers blends of only parabens as 'Nipastat' and 'Nipasept', Cognis's Elestab FL 15, Elestab 48, Elestab 50J, Elestab 305, Elestab 388, Elestab 3344, Elestab 4112, Elestab 4121, Elestab 4150 Lipo are all blends of antimicrobials with at least one paraben in them. Induchem's Uniphen P23, ISP's Germaben and LiquaPar series of blends contain several parabens. Galaxy Surfactants offers Galguard NK1 and Galguard NK2 blends that are based on four and five paraben blends respectively with phenoxy ethanol. Five blends by McIntyre/Rhodia from their 'Paragon' series have several parabens. Neolone MXP of Rohm and Haas has parabens with methyl isothiazolinone. Neo-Dragocide series of blends from Symrise has parabens. Euxyl K 300 of Schulke and Mayr has five parabens. Thor's Microcare PM4 and Microcare PM5 have four and five parabens respectively. What it shows is that the parabens are doing a great job of being good preservatives.

All phenolic antimicrobials have phenolic 'hydroxyl' group and that is a very reactive organic functionality with very acidic hydrogen with pKa of 10. Parabens are phenol derivatives and the other compounds as mentioned above are widely used. However, during 1998 to 2004 a few scientific publications implicated parabens in endocrine disrupting estrogenic activity and some other deleterious effects on reproductive systems in various test methods. [(Pedersen, K. L. et al., *The preservatives ethyl-, propyl-and butylparaben are estrogenic in an in-vivo fish assay, Pharmacology & Toxicology* (Vol. 86(3), pp 110-13, March 2000); Routledge, E. J., et al., *Some alkyl hydroxy benzoate preservatives (parabens) are estrogenic, Toxicology and Applied Pharmacology* (Vol. 153(1), pp. 12-19 (November 1998); and Kang, K. S. et al, *Decreased sperm number and motile activity on the F 1 offspring maternally exposed to butyl p-hydroxybenzoic acid (butyl paraben), Journal of Veterinary Medical Science* (Vol. 64(3), pp. 227-35 (March 2002); and Philippa Darbre and Philip Harvey, *Endocrine disrupters and human health: could estrogenic chemicals in body care cosmetics adversely affect breast cancer incidence in women, Journal of Applied Toxicology,* 24 (3): 167-176, (2004)].

In view of these scientific publications, in 2005 Cosmetic Directive of EU reexamined the severity and fixed the maximum usage levels of parabens for topical applications. However, this clean chit does not seem to be adequate to mitigate the grave concern about the usage of parabens as preservatives. The stigma on paraben continues and personal care industry is asking for preservatives that are free of parabens.

Formaldehyde Releasing Antimicrobials:

Formaldehyde is classified as Category 3 CMR (carcinogenic, mutagenic and reproductive toxicity). However, it is interesting to note that a few antimicrobials that slowly release formaldehyde are still being used and being commercially manufactured. Due to the paucity of effective and well-accepted antimicrobials, the industry is forced to continue with the using formaldehyde donors like DMDM hydantoin, imidazolidinyl urea, and diazolidinyl urea. The formaldehyde released by these substances is capable of reacting with several cosmetic ingredients via its very reactive aldehydic carbonyl functionality. For example, the only available and globally approved UV-A absorber, Avobenzone, reacts with formaldehyde that is released by formaldehyde derivatives. This is a big disadvantage for sunscreen formulations. Preservative blends, Clariant's Niapaguard PDU and Cognis's Elestab 305, ISP's Germaben II, Germaben H-E, exploit combinations of parabens with diazolidinyl urea. ISP's Germall Plus and Lonza's Glydant Plus have diazolidinyl urea along with iodopropynyl butyl carbamate (IPBC) in them. McIntyre's Paragon series has DMDM hydantoin and other antimicrobials like paraben, phenoxy ethanol and IPBC. Symrise's Neo-Dragocide and Thor's Microcare IMP exploit synergy between parabens and imidazolidinyl urea.

Quaternary Ammonium Antimicrobials:

The third category of the quaternary ammonium compounds (examples are cetyl pyridinium chloride, benzethonium chloride, benzalkonium chloride, polyaminopropyl biguanide), has been of limited use for personal care industry due to specific incompatibilities with other cosmetic ingredients.

Lonza's Geogard series of preservative blends avoids use of parabens in their new creations (Geogard 233S, Geogard 233S, Geogard 233S, Geogard 361) however, these antimicrobial compositions are based on cationic benzethonium chloride which gets deactivated by many anionic ingredients that form important part of topical personal care formulations.

Halogentated Antimicrobials:

Nalco's Merguard series (four blends) banks on halogenated molecules, methyl dirbromo glutaronitrile and 2-bromo-2-nitro-1,3-diol. Several blends of Euxyl series from Schulke and Mayr are based on chlorothiazolinones, methyl dibromo glutaronitrile, 2-bromo-2-nitro-1,3-diol and diazolidinyl urea. Microcare series from Thor employs parabens, 2-bromo-2-nitro-1,3-diol, iodopropynyl butylcarbamate (IPBC), imidazolidynyl urea, and diazolidinyl urea.

The other examples of halogenated antimicrobials are chlorphenesin, and chlorhexidine. It is common knowledge that like phenolic compounds, the halogenated organic molecules exhibit significant levels of toxic effects. For example, IPBC has risk of thyroid hormonal disturbances due to its iodine content. It has not been allowed in Japan and in EU it is allowed only up to 0.02% in leave-on products. Similarly EU permits usage of methyl dirbromo glutaronitrile only up to 0.1% and that too in only rinse-off products. Bronopol, 2-bromo-2-nitropropane-1,3-diol, is implicated in generation of carcinogenic nitrosoamines on interacting with some of the nitrogen containing cosmetic ingredients. Methyl chloro isothiazolinone is so powerful antimicrobial that it is allowed only in rinse-off products at 15 ppm concentration. Chloromethyl isothiazolinone does have a very broad spectrum of anti-microbial activity. But the toxicity of such powerful anti-microbials is extremely high and hence cosmetic formulators do not prefer to use this kind of powerful antimicrobial in the cosmetics that remain on human skin for a long time. It is reasonable to expect that any thing that is strong bactericidal at a low concentration (ppm level) is likely to be equally lethal to any other cells of a living organism, including human cells. This is the precise reason why in Japan chloromethyl isothiazolinone is not allowed for preservation if the product is going to come in contact with the mucous membrane.

In spite of these serious concerns associated with the four major categories of antimicrobials that are used as preservatives, the cosmetic formulators have no choice but to continue using whatever is available. The manufacturers have been selling the blends of 2 to 5 antimicrobials in order to increase the efficacy through the synergy. However, almost all effective antimicrobial blends offered by the leading world manufacturers either contain a paraben or a formaldehyde donor or a halogenated molecule ('*Preservatives for Cosmetics*' by David Steinberg, Allured Publishing Corporation, $2^{nd}$ Ed, 2006).

The consumer concern about parabens and formaldehyde releasing antimicrobials and the industry's continuous search for a new safe antimicrobial as well as new blends and combinations to address the current needs have been nicely covered in a 'Preservative Update' by Tom Branna, in Household and Personal Products Industry (HAPPI), May issue (2006). So far there is very little success with the search of a new safe ideal molecule and all the major manufacturers of antimicrobial preservatives for cosmetics continue to manufacture and sell preservative blends with either parabens or with formaldehyde donors. As mentioned in the foregoing discussion on the blends, commercial synergistic blend with trade name of 'Phenonip' by Clamant is nothing but parabens with phenoxy ethanol. Similarly, 'Germaben II' of ISP is a commercial blend of diazolidinyl urea with parabens, Lonza's 'Glydant Plus' has DMDM hydantoin. McIntyre's Paragon PPM has all five parabens with phenoxy ethanol, so does Microcare PM-5 by Thor. Euxyl K300 by Schulke and Mayr, Galguard NK1 & 2 from Galaxy Surfactants as well as Neolone MXP from Rohm and Haas too has parabens with phenoxy ethanol.

Preserving personal care products from microbial degradation is quite challenging. Most topical cosmetics and dermatological products, in the form of creams, lotions, gels, shampoos, body washes, face washes contain significant amount of water in them that provides a very hospitable environment for the microbial growth. In addition to water, the other cosmetic ingredients can also be a good source of nutrients to microbes. Another pertinent point to be reckoned here is that the shelf-life of the personal care products and the period after opening the container by the consumer is quite long compared to pharmaceutical products or food products. Unlike pharmaceuticals, cosmetics products are neither sterilized and nor packed in hermetic conditions. Thus, the requirement for the preservation of the personal care products is indeed quite challenging. This is further compounded by the limited choice of antimicrobials. Most antimicrobials available today for preservation of personal care products are not the ideal ones. The consumer's awareness is very high and expects the preservatives in personal care products to be not only effective but extremely mild on the person since one uses personal care products life long. In recent years, a host of non-government organizations (NGOs) have targeted parabens and other preservative systems that include formaldehyde donors, halogenated organic molecules and phenolic compounds. Bad press (suspected endocrine disrupting activity) for the parabens forced antimicrobial manufacturers and the cosmetic industry to search for the alternatives to paraben.

The manufacturers of preservatives and personal care industry are looking for better and safer alternatives. Though discovering a new powerful and toxicologically safe broad spectrum antimicrobial is possible, it is a long and expensive process to discover new material and have it approved by the Cosmetics Directives and accepted by the global markets. According to the experts in industry an 'ideal preservative' is like "Holy Grail" and the industry has stopped looking for the 'ideal' preservative. (Donald Orth in 'Insights into cosmetic microbiology', Allured Publications, 2010).

Thus, faced with a consumer rebellion against certain categories of preservatives, much of the current effort by the industry has been directed in discovering synergy between mixtures of existing preservatives and in finding personal care ingredients that may have a coincidental antimicrobial activity (John Woodruff, *Soap Perfumery and Cosmetics*, September, 2006).

Recently Arch Personal Care, USA, invented MicroKill COS and MicroKill PCC that are based on chlorphenesin and chloroxylenol respectively. It is to be noted that these preservatives are free from parabens and free from formaldehyde releasers but they are halogenated molecules. Lonza's recent commercial introductions commercial are Geogard 2333, Geogard 2355, and Geogard 361 are based on benzethonium chloride, a quaternary ammonium compound. ISP's latest invention is Liquagard which is nothing but iodopropynyl butyl carbamate (IPBC), again a halogenated molecule. Vertellus Specialities, Italy, launched ZeStat that is again a quaternary ammonium surfactant, cetyl pyridinium chloride.

In order to get rid of formaldehyde donors and halogenated molecules International Specialty Products, USA, came up with 'Octiphen' which is a combination of phenoxy ethanol and caprylyl glycol. Schulke and Mayr, Germany, launched the preservative blends Euxyl K600, K700 and K702 that are free of formaldehyde donors, parabens and halogenated compounds. These are based on combinations of organic acids like dehydroacetic acid, benzoic acid and formic acid.

Octiphen BSB-N from ISP is a combination of benzoic acid, sorbic acid and benzyl alcohol. Similarly Sharon MX 705 is a blend of sorbic acid, benzyl alcohol, benzoic acid and dehydroacetic acid.

In summary, the antimicrobial manufacturers do not seem to be looking to invent the 'ideal' preservative but synergistic combinations of antimicrobials to avoid parabens or formaldehyde donors. However, in most cases one can see quaternary compounds or halogenated molecules form the important constituents of the antimicrobial blends where parabens and formaldehyde donors have been omitted. In other cases the combination of organic acids are being used. A limitation of low molecular weight organic acids is that they are effective in acid form and hence only at low pH show efficacy as antimicrobial preservative. For example, benzoic acid is effective if it remains as benzoic acid and loses it efficacy in its 'benzoate' form.

There have been some attempts to create synergistic blends avoiding parabens and formaldehyde donors have been reported. For instance, in 2008, Ellen Rozsa et al. reported a synergistic preservative system having an oil-miscible glycol and an enzymatic composition (U.S. Pat. No. 226,568, 2008). The synergistic preservative system of this patent application demonstrates enhanced anti-fungal, anti-bacterial, and anti-microbial efficacy and is free of formaldehyde donors, parabens, and isothiazolinones. However, again, using enzymatic compositions as preservative for personal care product may not be globally accepted since the enzymes used are glucose oxidase and lactoperoxidase.

Although several undecylenic acid derivatives have been reported to possess some antifungal activity, these have not been exploited commercially for the preservation of personal care formulations. For example, undecylenoyl glycine is reported to possess anti-acne activity, (CAS No 54301-26-7, EINECS No 427-430-5) when used along with other ingredients like zinc gluconate, capryloyl glycine, plant extracts from rathania, tea, cinnamon, willows or hamemelis (EP 0983055131). However, the significant limitation of using lipidated amino acid like undecylenoyl glycine is that they show effectiveness only when present in carboxylic acid form. When pH is more than 7 then part of it goes in the salt form (carboxylate form) and it loses its efficacy. This is a severe limitation that pH of the cosmetic formulation has to be on the acidic side (WO 99/27902/EP 0983055B1).

Interestingly, in 2004 use of combination of Wasabi extract along with undecylenoyl glycine (lipidated amino acid) as a co-preservative for protection of personal care preparations was reported by D. Misner (US 2004096528A1). This is the sole instance from the prior art that suggests use synergistic combination of undecylenoyl derivatives with other ingredients for the purpose of preservation.

The present invention overcomes this limitation by creating preservative systems that have antimicrobial undecylenoyl derivative that remains active over a broad pH range.

In summary, personal care industry has limited choice of anti-microbial agents that can be safely used for preservation of formulations that are accepted by the end consumers. The personal care industry is looking for an absolutely non-toxic, safe and broad spectrum anti-microbial that would be acceptable by the consumers all over the world. Other important and essential criterion is that the preservative system made up of either a single antimicrobial substance or a blend should be completely compatible with commonly used cosmetic ingredients. These requirements are not easily addressed by designing a new antimicrobial molecule because it takes at least a decade before a globally accepted molecule is born.

In view of the absence of an 'ideal' antimicrobial and the current unavailability of safe, effective and non-controversial preservation systems, there is an urgent need to meet this requirement from 'synergistic' combination of established personal care ingredients that are 'very safe and mild' and that would give broad range of protection (effective against Gram positive and Gram negative bacteria, yeast and mould) and be free of formaldehyde donors, free of halogenated molecules and phenolic molecules and quaternary ammonium compounds and that would be acceptable to the global community. Thus, despite the growing concerns, the personal care industry is forced to use parabens, formaldehyde donors and halogenated compounds. This is simply because there is no effective and efficacious alternative preservative system available that would replace them. Preservative industry's efforts in this direction have been met with little or no success at all.

Hence there was a need to provide an efficient preservation system comprising synergistic combination of preservatives for personal care formulations.

The present invention thus provides a preservative combination made up of very 'safe and nontoxic' personal care ingredients and that are free from parabens, formaldehyde

OBJECTS OF INVENTION

It is an object of the present invention is to overcome the drawbacks of the prior art.

It is another object of the present invention to provide a three component synergistic preservative blend of antimicrobial preservation composition for personal care formulations.

Yet another object of present invention is to provide an economic and cost effective preservation system.

SUMMARY OF THE INVENTION

According to one aspect of the present invention, there is provided a preservation composition for personal care formulations comprising [A] one or more undecylenic acid derivatives depicted by Formula (I), wherein, M=NH—CH$_2$—OH NH—CH$_2$CH$_2$—OH, N—(CH$_2$CH$_2$—OH)$_2$, NHCH$_2$CH$_2$CH$_2$N(CH$_3$)$_2$, NHCH$_2$CH$_2$CH$_2$N(CH$_3$)$_2$→O, NHCH$_2$CH$_2$CH$_2$N$^+$(CH$_3$)$_3$CH$_3$SO$_4$$^-$ NHCH$_2$CH$_2$CH$_2$N (CH$_3$)$_2$CH$_2$—CH$_2$N$^+$(CH$_3$)$_2$—CH$_2$COO$^-$ NH—CH$_2$CH$_2$—CH$_2$N$^+$(CH$_3$)$_2$—CH$_2$(OH)CH$_2$CH$_2$SO$_2$O$^-$, OCOR' (R'=alkyl group with C1 to C18), O—CH$_2$CH$_2$—OH, O—CH(OH)CH$_2$—OH, O-poly-ol O—CH$_2$CH$_2$—OR' (R'=undecylenoyl), O—C(CH$_3$)$_2$—OH, protein (animal or vegetable derived) hydrolyzate (through nitrogen end), NH—CH$_2$CH$_2$—O—(O—CH$_2$CH$_2$)$_n$—CO(CH)—COONa)—CH$_2$—(SO$_3$Na), n=0 to 3,

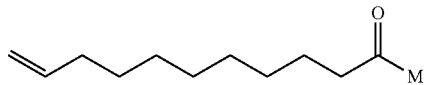

Formula I

[B] one or more octanoic acid derivatives depicted by Formula (II), wherein, M=NH—CH$_2$—OH, NH—CH$_2$CH$_2$—OH, N—(CH$_2$CH$_2$—OH)$_2$, or NH—CH$_2$COOH and [C] 2-phenoxy ethanol or 2-ethyl hexyl glyceryl ether or mixture of these two 'liquid alcohol ethers', wherein, each of the two components [A] and [B] is present in the range of 5 to 20% by weight and together [A] and [B] constitute 10 to 30% by weight and the 'liquid alcohol ether' component [C] is present 70 to 90% by weight of the total composition.

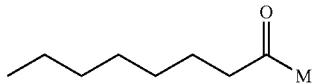

Formula (II)

According to another embodiment of the invention, there is provided personal care products that are protected from the microbial contamination by the synergistic preservative systems is selected from emulsions, gels, serums, solutions, toners, lotions, creams, spray, gel, powder, stick and cleansers for topical application.

According to another embodiment of the invention, there is provided a 'three component' composition for preservation of personal care products comprising of undecylenoyl derivatives, N-octanoyl derivatives and 'liquid alcohol ethers' for broad spectrum antimicrobial activity.

DETAILED DESCRIPTION OF THE INVENTION

The present invention provides a synergistic combination of cosmetic ingredients comprising a) non-phenolic, b) non-halogenated and c) non-formaldehyde releasers to preserve personal care formulations. All the components of the combination are safe and completely biodegradable substances that are widely used by personal care industry.

The inventors of present invention have found that the combination of preservation system shows synergistic effect in terms of the antimicrobial effect even at lower concentration in comparison with the individual substances.

The present invention provides novel combinations of surfactants with undecylenic chain as the hydrophobe (Formula I) and surfactants with octanoyl chain (Formula II) as the hydrophobe along with 'liquid alcohol ethers' like 2-phenoxy ethanol or 2-ethyl hexyl glyceryl ether. The hydrophobic portion is provided by either octanoyl (C8) or undecylenoyl (C10) chains and the hydrophilic portion is provided by either by hydroxyl/carboxyl groups or ionic groups like sulphonate, sulphosuccinates or quaternary ammonium groups.

The 'liquid alcohol ether' as used herein like 2-ethyl hexyl glyceryl ether is also a surfactant where the hydrophobe is provided by octyl group and the hydrophilic portion is the two hydroxyl groups of glycerine moiety and the ether linkage. It is reported HLB value is 7.5 and it shows good surface activity and reduces surface tension of water from 72 dynes/cm to 32 dynes/cm at 0.1% aqueous solution at 25° C. This surface active behaviour is very similar to the one exhibited by N-octanoyl monoethanol amide which also reduces the surface tension of water to 38 dynes/cm at 0.05% level.

Suitable concentration of the 'three component' preservative systems of the present invention may vary according to the personal care product formulation that is being preserved depending upon the amount of water in the formulation. It varies from 0.5% to 2.5% by weight of the total topical formulation. The MICs (minimum inhibitory concentration) against a variety of microbes for the 'three component' blend is lower than the individual constituents. The antimicrobial efficacy of their preservative blends was 'challenge tested' through a variety of formulations and against a variety of microbes to determine the efficacy of the blends.

Present invention teaches use of one or more undecylenic acid derivatives (Formula I), component [A], as one of the three components of the preservative system. There are a number of cosmetic ingredients derived from undecylenic acid that are commercially available. In general, undecylenoyl derivatives are being used as cosmetic biocide, foam booster, viscosity booster, conditioner, anti-dandruff, and in antifungal applications in foot powder and underarm deodorant stick.

The personal care ingredients based on undecylenic acid listed in the International Cosmetic Ingredient Directory and Handbook (13$^{th}$ edition, 2010) are undecylenlamide MEA and undecylenlamide DEA, undecylenoyl MEA sulphosuccinate, undecylenoyl amidopropyl betaine, glucosyl undecylenate, undecylenoyl PEG-5 paraben (antimicrobial), undecylenoyl phenylalanine (skin conditioning agent), undecylenoyl serine/silk amino acid methyl ester (hair skin and nail conditioning agent), undecylenoyl wheat amino acid (surfactant), undecylenoyl collagen amino acid, undecylenamidoproppyl trimonium methosulpahte (antistatic hair conditioner), undecylenamidopropyl amine oxide (cleansing agent, foam booster), undecylenamidopropyl betaine (foam booster, viscosity booster, skin and hair conditioner) undecylenamido propyl PEG-2 dimonium undecylenate (anti-dandruff agent) undecylenoyl hydrolyzed collagen, undecylenoyl grape seed extract, undecylenoyl xanthan gum (hair conditioner) and esters with various monohydric and polyhydric alcohols like monohydric small to medium chain, branched or unbranched alcohols.

The present invention provides a preservative system that is based on undecylenoyl derivatives that are not affected by the variation in the pH. The examples of such undecylenic derivatives are the alkanol amides of undecylenic acid. Alkanolamides of undecylenic acids are non-ionic surfactants that have disinfecting properties (HU 9800933A2). Undecylenoyl monoethanol amide (CAS 20545-92-0) is used in several topical applications that deal with fungal infection of skin (Cosmetologic de Harry by J. B. Wilkinson, R. J. Moore, Marta Rodriguez Navarro). Commercially, it is available by the trade name of Fungicid UMA from Dragacco. Undecylenoyl diethanol amide (CAS No 60239-68-1) is commercially available as Rewocid DU 185SE from Evonik-Goldschmidt (Handbook of preservatives by Michael Ash and Irene Ash, 2004). In addition to the alkanol amides of undecylenic acid, the disodium undecylenaamido MEA sulphosuccinate, an anionic surfactant, also shows phenomenal anti-microbial activity. U.S. Pat. No. 3,385,755 reports marked antifungal activity of this sulphosuccinate surfactant of undecylenic acid along with others particularly against *Tricophytum mentagrophytis* and *Pityrosporum ovale*. It is available as Rewocid SBU from Evonik-Goldschmidt. Similarly, undecylenamidopropyl trimonium methosulphate, a quaternary ammonium surfactant, commercially available as Rewocid UTM 185, exhibits powerful antifungal activity.

Formula I

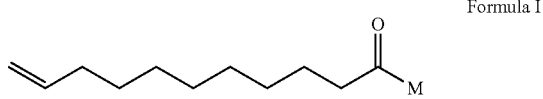

Undecylenic component, component [A] of Formula (I) is selected from undecylenic monoethanol amide, undecylenic diethanol amide, undecylenoamidopropyl betaine, undecylinoamidopropyl hydroxyl sultaine, undecylenamidopropylamine oxide, undecylenamidopropyl trimonium methosulphate, undecylenamidopropyl PEG-2-dimonium undecylenate, undecylenic monoethanol amide sulphosuccinate, N-undecyleno protein hydrolyzate, ethylene glycol mono and di-undecylinate and in general, any ester made from polyol and undecylenic acid. The polyols that can be employed for the esterification of undecylenic acid can be selected from glycerine, neopentyl glycol, and pentaerythritol.

The second component, [B], in these 'three component' preservative systems of the present invention is the N-octanoyl derivative of Formula II. They are mainly two types of non-ionic surfactants N-octanoyl alkanol amides and N-octanoyl glycine. For Formula (II)

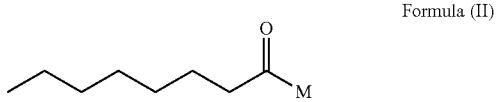

example, N-octanoyl MEA amide (CAS No 7112-02-9, N-(2-hydroxylethyl)caprylic acid amide) is very much the part of cocomono ethanol amide (CAS 681-40-001, EINECS No 268-770-2) and cocodiethanol amide (CAS No 68603-42-9, EINECS No 271-657-0) that are used by the personal industry on a huge scale for viscosity build up or as a rheology modifier. These alkanol amides are mixtures of alkanol amides with hydrophobic alkyl chain ranging from C8 to C18, derived from coconut or palm kernel fatty acids. Usually, C 8 and C 10 based alkanol amides in commercially available coco-fatty acid based alkanol amide range from 4% to 12%. This is the percentage range these occur in nature in coconut oil or palm kernel oil. Individually, N-octanoyl MEA amide, is a surface active agent and reduces surface tension of water to 30 dynes/cm at 0.1% concentration. Its synthesis was first reported by D'Alelio, G. F.; Reid, and E. Emmet in *Journal of the American Chemical Society* (1937).

N-Octanoyl glycine (CAS No14246-53-8) is again a well-accepted and well-known skin purifier/protector. Commercially, it is available as Lipacide C8G from SEPPIC, France. It is active against most of the natural resident micro-flora that reside on human skin and is used in anti-acne, antiperspirant and deodorant preparations. (Table I).

These two components, [A] undecylenic acid derivatives and [B] N-octanoyl derivatives are then dissolved at room temperature or with slight warming up to 40° C. in component [C] 'liquid alcohol ether' like other 2-phenoxy ethanol or 2-ethyl hexyl glyceryl ether or a combination of the two to afford cosmetically acceptable synergistic preservative systems for personal care products.

In the proposed blends of this patent application each of these two components [A] and [B] is present from 5 to 20% by weight, preferably in the range of 10 to 20%, by weight, of the total composition. The third constituent [C], the liquid alcohol ether, may be selected from phenoxy ethanol, 2-ethyl hexyl glycerol. The 'liquid ether alcohol' can be employed alone or a blend of the two along with N-octanoyl component [B] and an undecylenic acid component [C]. The third constituent [C] is present from 70 to 90%, preferably, 70 to 80%, of the total preservative composition. Alcohol ethers are colorless, non-volatile liquids that have very good solvent properties. They themselves are not strong antimicrobial and certainly do not provide the broad spectrum of anti-microbial activity and normally used in high concentration if used alone. This is the precise reason why are they usually combined with other antimicrobials to provide a broad spectrum of activity. These 'liquid alcohol ethers', although weak, are well established and offer additional benefits like moisturization of skin due to its ability to bind with water through the ethereal oxygen and the hydroxyl functionality. 2-Ethyl hexyl glycerine is a good moisturizer and a medium-spreading emollient. In fact, it is described as multifunctional cosmetic ingredient. It helps in improving the sensory properties of the cosmetic formulations. It is active against bad odour causing Gram positive bacteria (CAS No 70445-33-99, EINECS No 408-080-2). It is a cosmetic ingredient and is used in deodorant formulation to boost activity of the other antimicrobials and is commercially available from Schulke and Mayr under the trade name of Sensiva SC 50. 2-Ethyl hexyl glyceryl ether does not have significant antimicrobial activity; however, it is reported to boost antimicrobial activity of other substances (EP 0747047A, 1976 and U.S. Pat. No. 5,736,574, 1998).

The other 'liquid alcohol ether' of the component [C] that is used in the preservative blends of the present application is 2-Phenoxy ethanol. It occurs in the nature (Chinese Green Tea) and has been consumed by human race for centuries. 2-Phenoxy ethanol (CAS No 122-9-6, EC No: 204-589-7) was used as anti-microbial to treat the open wounds of soldiers in World War II. It is a gentle antimicrobial and is preferred in preserving vaccines that contain very labile proteins. 2-Phenoxy ethanol is active against Gram negative bacteria (Cosmetic and Drug Preservation, Principles and Practice, Vol I, Ed Jon Kabara, Marcel Dekker), however, it shows very weak activity against Gram positive and virtually no activity against fungi. However, in the synergistic formulation of the present invention the broad protection can be easily achieved by mixing the above mentioned three constituents in the right proportion.

In summary, the 'three component' blends of this patent application are based on well accepted, safe, cosmetic ingredients that boost each other's potency synergistically. These are designed to be economical and offer broad spectrum of activity and are easy to incorporate and their antimicrobial efficacy has been established by MICs, Time Kill Study and challenge tests performed on the various personal care formulations by introducing fresh inoculums of microbes.

According to another embodiment of the invention the personal care products that are protected from the microbial contamination by the synergistic three component systems can be of any type of such as emulsions, gels, serums, solutions, toners, lotions, creams, spray, gel, powder, stick and cleansers for topical application.

The topical formulations according to the present invention may additionally contain further ingredients or additives such as solvents, surfactants, emulsifiers, rheology modifiers, conditioners, emollients, skin caring ingredients, other preservatives, thickeners, lubricants, fillers, antioxidants, other preservatives, active ingredients, in particular dermatologically active ingredients, fragrances and the like as well as mixtures thereof.

Suitable concentration of the 'three component' systems of the present invention may vary according to the personal care product formulation that is being preserved depending upon the ingredients used and the amount of water in the formulation. It varies from 0.5% to 2.5% by weight of the total topical formulation.

Advantages of 'Three Component' Combinations of Present Invention

1) The 'three component' synergistic preservative blends for the protection of topical products described in the specification selected are not only non-formaldehyde donors, non-halogenated, non-phenolic compounds but also non-parabens.
2) The preservative systems of present invention do not contain any 'formaldehyde releasing' substances.
3) The 'three component' preservative systems are free of halogenated (chlorinated, brominated, iodinated and fluorinated) antimicrobial molecules.
4) The 'three component' systems of this patent application are based on the personal care ingredients that are cosmetically well accepted, with proven benefits (surface active agents, rheology modifier, moisturizing effect, emollients, reduction in trans-epidermal water loss, dermopurifier effect, anti-acne and anti-dandruff) and are completely biodegradable.
5) All ingredients that are used in creating these 'three component' systems are extremely mild on skin and are reported as 'safe' for the skin care by 'Skin Deep Cosmetic Safety Data Base.'
6) The 'three component' systems exhibit synergistic antimicrobial activity. These blends offer broad range of antimicrobial activity at fairly low concentration. Minimum inhibitory concentration of the blends against all types of microbes ranges from 0.2 to 0.4%.
7) The 'trident' systems are based on the synergistic effect against the microbes but individually these are extremely mild substances toward human skin.
8) The compositions are designed to obtain the wide range of antimicrobial activity. The preservative compositions of this patent application blends are active against Gram positive, Gram negative bacteria, yeast and mould.
9) The 'three component' preservative systems of this patent application inhibit the growth of some of the most resistant Gram positive bacterium like *B. subtilis* at very low concentration.
10) Additional benefit of dermo-purification in case of 'leave-on' products is expected at the levels at which these blends are used as preservatives. The antimicrobial activity of the blends of the present invention covers the microbes that are not only commonly found in personal care formulations but also the microbes that are usual residents of human skin/body. For example, *Propionibacterium acnes*, an ubiquitous organism on human skin, is killed by the preservative blends of this patent application at 0.3% level. Another dandruff causing microorganism, *Melassezia furfur*, found on the skin of 75 to 98% of healthy people is completely destroyed at 0.4% concentration. The 'three component' blends of this patent application are effective against this normal flora that resides on human skin at 0.3% to 0.4% level. Thus, these compositions not only offer excellent preservation of personal care product but they act like dermopurifier maintaining good health of skin.
11) The 'three component' preservative blends are compatible with all cosmetic ingredients, stable towards any oxidizing or reducing agents and to normal range of pH (4.5 to 8.0) of personal care formulations.
12) The preservative blends of this patent application are made from personal care ingredients. The component [C], the liquid alcohol ether is the largest component, ranging from 70 to 90% of the total blend composition. Component [C] is made up of 2-phenoxy ethanol and 2-ethyl hexyl glyceryl ether. Phenoxy ethanol is produced world wide on thousands of metric tonne level and is one of the cheapest ingredients. Ethyl hexyl glycerine is also made on large scale from octanol and glycerine. The other surfactants that are used in component [B] and [C] are based on octanoic acid and undecylenic acids and are easy manufacture with straightforward established synthesis without using any complex non-eco-friendly chemistry. This makes these 'three component' preservative systems very economical. The compositions also designed to give best broad spectrum performance at the least of the cost.

The working of the said composition is illustrated by the following non limiting illustrative examples.

Example 1

Phenoxy ethanol was obtained from Galaxy Surfactants Ltd, Mumbai, India. 2-Ethyl hexyl glycerol (3-(2-ethyl hexyl)oxy 1,2-propanediol, trade name Sensiva SC-50) was procured from Schulke and Mayr, Germany. Undecylenic acid and octanoic acids were obtained from VVF Ltd, India. All other chemicals were purchased from Aldrich.
Synthesis of Surfactants:

N-undecylenoyl monoethanol amide, N-octanoyl glycine, and N-octanoyl monoethanol amide were synthesized in according to the procedures given below.
Preparation of N-Undecylenoyl Monoethanol Amide (MEA Amide of Undecylenic Acid):

A mixture of undecylenic acid (500 g, 2.71 mol) and monoethanol amine (166 g, 2.71 mol) is stirred under nitrogen blanket in pressure vessel at 140° C. for 4 hr and then the temperature is raised to 165° C. for additional one hour. At this stage, acid value is normally found to be around 10° C. or less. Cool the reaction mass to 60° C. and the molten mass are converted into off white flakes (610 g, 99%) by pouring it on glass plate. (Melting point 56-58° C., acid value, less than 10, IR (KBr):1640 cm$^{-1}$ carbonyl amide, 1556 cm$^{-1}$, 2919 cm$^{-1}$, 3289 cm$^{-1}$ (NH of amide).

Preparation of N-Octanoyl Monoethanol Amide (MEA Amide of Octanoic Acid):

A mixture of octanoic acid (114 g, 0.1 mol), BHT (0.3 g) and monoethanol amine (61 g, 0.1 mol) is stirred under nitrogen blanket in a pressure vessel at 140° C. for 4 hr and then the temperature is raised to 165° C. for additional one hour. At this stage, acid value is normally found to be around 5 or less. The reaction was then cooled under mild vacuum to 60° C. and the molten mass is converted into off-white flakes (148 g, 95%) by pouring it on a glass plate. (Melting point 62-64° C., acid value 5, IR (KBr):1640 cm$^{-1}$ (carbonyl of amide), 1556 cm$^{-1}$, 2919 cm$^{-1}$, 3289 cm$^{-1}$ (NH of amide) Reduction is surface tension of water: 0.05% solution, 38.5 dyne/cm, 0.1% solution 30.5 dyne/cm.

Preparation of N-Octanoyl Glycine:

To a cooled (15° C.) and stirred mixture of glycine (152 g, 2.0 mol), and water (1255 g) under nitrogen, N-octanoyl chloride (300 g, 1.84 mol) and sodium hydroxide (319 gm, 3.88 mole) are added and slowly and simultaneously while maintaining the pH of the reaction at around 10.0 to 10.5 and temperature around at room temp. After completion of the addition, the reaction mass is stirred for additional one hour. It is then acidified with hydrochloric acid and cooled to 20° C. N-Octanoyl glycine separates as white solid that is filtered and washed with copious amount of water to free it from mineral acidity. (M.P. 102-104° C. IR (KBr): 1697 cm$^{-1}$ carbonyl of COOH, 1641 cm$^{-1}$ carbonyl of amide, 3310, 3060 cm$^{-1}$, 2963, 2922 cm$^{-1}$)

Example 2

Preparation of Preservative Blends

General procedure for making the Preservative Blends: A mixture of components [A], [B] and [C] were stirred in the desired ratio of weight % under nitrogen blanket at 40° C. till a clear solution was obtained. It was then cooled to room temperature.

Preservative Blend No 1:
[A] N-decylenic acid MEA amide: 10%
[B] N-octanoyl glycine: 10%
[C] 2-phenoxy ethanol: 80%
Preservative Blend No 2:
[A] N-decylenic acid MEA amide: 10%
[B] N-octanoyl monoethanol amide: 10%
[C] 2-phenoxy ethanol: 80%
Preservative Blend No 3:
[A] N-decylenic acid MEA amide: 15%
[B] N-octanoyl glycine: 15%
[C] 2-phenoxy ethanol: 70%
Preservative Blend No 4:
[A] N-undecylenic acid MEA amide: 4%
[B] N-octanoyl monoethanol amide: 4%
[C] 2-Phenoxy ethanol: 92%
Preservative Blend No 5:
[A] N-undecylenic acid MEA amide: 25%
[B] N-octanoyl monoethanol amide: 25%
[C] 2-Phenoxy ethanol: 50%
Preservative Blend No 6:
[A] N-decylenamidopropyl betaine 10% and undecylenic acid MEA amide 10% each
[B] N-octanoyl glycine 10%
[C] 2-ethyl hexyl glyceryl ether 70%

Preparation of Gelatine Hydrolyzate:

A mixture of gelatine (262 g), subtilisin enzyme (protease (Alcalase 2.4 L from Novozymes 15 g) and water (487 g) was stirred under nitrogen for 8 hr at 50° C. pH was maintained at 7.00 to 7.5 by addition of sod hydroxide solution throughout the course of reaction. At the end of 6 hrs the reaction mass was cooled and pH was adjusted to 4 using hydrochloric acid and continued for additional 1 hr. Finally pH was adjusted to 7.0 to give of protein hydrolyzate as pale yellow colored slightly viscous solution with 20% solids content. The gelatine hydrolyzate thus obtained was preserved with 1.0% of the Preservative Blend No 1 and then subjected to the 'challenge test'.

Example 3

The minimum inhibitory concentration of individual cosmetic ingredients against different microorganism is shown in table 1.

TABLE I

MINIMUM INHIBITORY CONCENTRATION OF INDIVIDUAL COSMETIC INGREDIENTS IN PPM

| Organism | Phenoxy ethanol | Octanoyl Glycine | Undecylenoyl MEA amide | Octanoyl MEA amide |
|---|---|---|---|---|
| *Staphylococcus aureus* ATCC 6538S. | 8500 | 3000 | >10000 | >10000 |
| *Pseudomonas aeruginosa* Immuno type IV | 4000 | 3000 | >10000 | >10000 |
| *Escherichia coli* ATCC 10142 | 6000 | 3000 | >10000 | >10000 |
| *Bacillus subtilis* ATCC 9372 | 4000 | 3000 | >10000 | >10000 |
| *Malassezia furfur* MTCC 1374 | 4000 | 3000 | >10000 | >10000 |
| *Aspergillus niger* | 9000 | 4000 | >10000 | >10000 |
| *Propionibacterium acnes* MTCC 1951 | 4000 | 3000 | >10000 | >10000 |
| *Candida albicans* ATCC 10231 | 6000 | 4000 | >10000 | >10000 |

The surfactant undecelenoyl MEA amide (Formula I, wherein M=NH—CH$_2$CH$_2$—OH), the component [A] is reported to have antifungal activity (Istvan Laczko, HU 9800933 A2), but the activity is too weak to be used as a preservative as shown in Table I, let alone the broad spectrum of activity. The said compound is not reported to possess any activity against both Gram positive and Gram negative bacteria. The compound does not exhibit any antimicrobial activity, neither against bacteria nor against yeast and mould up to 1.0% concentration.

The same is the case with N-octanoyl MEA amide, component (Formula II, M=NH—CH$_2$CH$_2$—OH) [B], another non-ionic surfactant, that did not exhibit any antibacterial activity up to 1% concentration. MIC numbers against eight microbes are given in Table I.

Another lipoamide with octyl chain, a non ionic surfactant, N-octanoyl glycine (Formula II, M=NH—CH$_2$COOH), is reported to have antimicrobial properties (EP 0747047B and U.S. Pat. No. 5,736,574). It was found to possess moderate activity against the broad range of microbes in the range 3000 to 4000 ppm concentration when tested at neutral pH. The 'liquid alcohol ether', component [C], 2-phenoxy ethanol is one of the mildest antimicrobial in personal care industry shows weak activity against bacteria particularly against Gram positive and virtually no activity against yeast and mould as shown in Table II.

TABLE II

MINIMUM INHIBITORY CONCENTRATION in PPM
Preservative Blend No 1
Concentration of individual component in ppm

| Organism | MIC | 2-Phenoxy-ethanol | Undecylenoyl MEA amide | Octanoyl Glycine |
|---|---|---|---|---|
| *Staphylococcus aureus* ATCC 6538S. | 2000 | 1600 | 200 | 200 |
| *Pseudomonas aeruginosa* Immuno type IV | 2000 | 1600 | 200 | 200 |
| *Escherichia coli* ATCC 10142 | 2000 | 1600 | 200 | 200 |
| *Bacillus subtilis* ATCC 9372 | 2000 | 1600 | 200 | 200 |
| *Malassezia furfur* MTCC 1374 | 4000 | 3200 | 400 | 400 |
| *Aspergillus niger* ATCC 16404 | 3000 | 2400 | 300 | 300 |
| *Propionibacterium acnes* MTCC 1951 | 3000 | 2400 | 300 | 300 |
| *Candida albicans* ATCC 10231 | 3000 | 2400 | 300 | 300 |

A combination of undecylenoyl MEA amide, component [A] and N-octanoyl glycine, component [B] and phenoxy ethanol, component [C] in the ratio of 10:10:80 by weight ([A]:[B]:[C]::10:10:80) as given in Preservative Blend No 1 (the experimental section) showed remarkable broad range of activity against all types of microbes including dandruff causing *Malassezia* and acne causing *Propionibacterium*. Phenoxy ethanol by itself has virtually no activity against *Aspergillus* and *Candida*, however, in combination with component [A] and [B] of the Preservative Blend No 1, in around 0.25% is enough to kill both organisms. Undecylenoyl MEA amide that shows no activity by itself up 10000 ppm concentration, however, in the synergistic Preservative Blend No 1, it is effective at 200 to 300 ppm to cover a broad range of microbes. The same is true for the other surfactant, octanoyl glycine too. By itself to be active that is to inhibit the growth of microbes, N-octanoyl glycine needs to be present in 3000 to 4000 ppm concentration to exhibit a decent level of antimicrobial activity but in a combination a mere 200 to 300 ppm concentration, almost one tenth of the concentration of an individual ingredient is required to be effective as represented in Table III.

TABLE III

MINIMUM INHIBITORY CONCENTRATION IN PPM
Preservative Blend No 2
Concentration of individual component in ppm

| Organism | MIC | 2Phenoxy-ethanol | Undecylenoyl MEA amide | Capryloyl MEA amide |
|---|---|---|---|---|
| *Staphylococcus aureus* ATCC 6538S | 3000 | 2400 | 300 | 300 |
| *Pseudomonas aeruginosa* Immuno type IV | 3000 | 2400 | 300 | 300 |
| *Escherichia coli* ATCC 10142 | 3000 | 2400 | 300 | 300 |
| *Bacillus subtilis* ATCC 9372 | 2000 | 1600 | 200 | 200 |
| *Malassezia furfur* MTCC 1374 | 4000 | 3200 | 400 | 400 |
| *Aspergillus niger* ATCC 16404 | 2000 | 1600 | 200 | 200 |
| *Propionibacterium acnes* MTCC 1951 | 2000 | 1600 | 200 | 200 |
| *Candida albicans* ATCC 10231 | 2000 | 1600 | 200 | 200 |

It is observed from Table III that almost similar results were obtained when N-octanoyl glycine of Preservative Blend No. 1 was replaced by N-octanoyl monoethanol amide. A combination of N-undecylenoyl MEA amide, component [A], N-octanoyl monoethanol amide, component [B] and phenoxy ethanol, component [C] in the ratio of 10:10:80 by weight ([A]:[B]:[C]::10:10:80) as given in Preservative Blend No 2 also exemplified in below given experimental section exhibited broad range of antimicrobial synergistic action at 0.2 to 0.3%. Manufacturing of Preservative blends having both amide of octanoic acid or undecylenic acid can be made in one pot synthesis. More or less similar results were obtained with Preservative Blend No 3 where the ratio on % weight basis was varied compared to Preservative Blend No 2 as shown in Table IV.

It was also observed that combination of 'three components' gave the best results at very moderate percentage of component [A] and component [B].

For example, binary mixtures 30% of undecylenoyl MEA amide and 70% of phenoxy ethanol or 30% of octanoyl MEA amide with 70% of phenoxy ethanol showed significantly inferior performance in terms of Minimum inhibitory concentration against the chosen eight organisms compared to the ternary mixture, the 'three component' system of Preservative Blend No 2.

Further Preservative blend No. 3 was compared with Preservative blend No. 2 based on percent weight ratio as shown in Table IV.

It was also observed that combination of 'three components' gave the best results at very moderate percentage of component [A] and component [B]. For example, binary mixtures 30% of undecylenoyl MEA amide and 70% of phenoxy ethanol or 30% of octanoyl MEA amide with 70% of phenoxy ethanol showed significantly inferior performance in terms of Minimum inhibitory concentration against the chosen eight organisms compared to the ternary mixture, the 'three component' system of Preservative Blend No 2.

TABLE IV

MINIMUM INHIBITORY CONCENTRATION IN PPM
Unedecylenoyl MEA amide, Octanoyl MEA amide and Phenoxy ethanol

| Organism | 10:10:80 Blend No 2 | 15:15:70 Blend No 3 | 4:4:92 Blend No 4 | 25:25:50 Blend No 5 |
|---|---|---|---|---|
| *Staphylococcus aureus* ATCC 6538S | 3000 | 3000 | 6000 | 5000 |

TABLE IV-continued

MINIMUM INHIBITORY CONCENTRATION IN PPM
Unedecylenoyl MEA amide, Octanoyl MEA amide and Phenoxy ethanol

| Organism | 10:10:80 Blend No 2 | 15:15:70 Blend No 3 | 4:4:92 Blend No 4 | 25:25:50 Blend No 5 |
|---|---|---|---|---|
| Pseudomonas aeruginosa Immuno type IV | 3000 | 4000 | 4000 | 7000 |
| Escherichia coli ATCC 10142 | 3000 | 4000 | 3000 | 4000 |
| Bacillus subtilis ATCC 9372 | 2000 | 3000 | 7000 | 10000 |
| Malassezia furfur MTCC 1374 | 4000 | 5000 | 9000 | 5000 |
| Aspergillus niger ATCC 16404 | 2000 | 4000 | 7000 | 5000 |
| Propionibacterium acnes MTCC 1951 | 2000 | 2000 | 6000 | 5000 |
| Candida albicans ATCC 10231 | 2000 | 2000 | 7000 | 5000 |

The three component systems exhibit optimum broad spectrum performance when the undecylenoyl component [A], octanoyl component [B] and the liquid alcohol ether [C] are present in a certain ratio. The maximum performance was obtained when [A] and [B] are present in the range of 5 to 20% by weight individually and together they should be present at 10 to 30% by weight in the final preservative blend. This can be seen from the results depicted in Table IV.

Preservative Blend No 4 comprises both components [A] and [B] present in 8% by weight and component [C] is present in 92% by weight. Compared to individual constituents there is still 'three component' synergistic effect. However, when performance of Blend No 4 was compared with Blend No 2 and 3, it was observed that MIC values against bacteria (Bacillus, Staphylococcus) and the fungi (Aspergillus, Candida) are quite inferior. The minimum inhibitory concentration required to restrict growth of Bacillus subtilis was found to be 7000 ppm compared to 2000 ppm of Blend No 2 and in case of Aspergillus the MIC was found to be 7000 ppm as compared to 2000 ppm for Blend No 2. Similarly, in case of Blend No 5, the component [A] and [B] are present in significantly high of 25% by weight individually, and component [C] is present at 50% by weight. In this blend too though the 'three component' synergy exists, it is far inferior to Blend No 1 and Blend No 2 (Table IV). Thus the 'maximum synergy' is obtained with certain range of individual components for the 'optimum antimicrobial broad spectrum effect'

It was also observed from the experiments conducted that further lowering percentage of 'liquid alcohol ethers', the component [C], and the consequent increase in the components [A] and [B] does not necessarily improve performance significantly. On the contrary it lowers the performance against Gram negative bacteria if phenoxy ethanol percentage is lowered. Similarly, lowering of ethyl hexyl glyceryl ether also lowers the performance against certain Gram positive bacteria. The synthesis ease of component [A] and [B] in any proportion if both are amides as in Preservative Blend No 2 since it can be done in one pot. Cost versus broad spectrum of activity these surfactant blends is further described in advantages of the present invention.

Further, the 'Time Kill Study' performed on these 'three component' preservative systems of the present patent application showed excellent results. Table V represents the results of Preservative Blend No 1. The study was carried with 1% Preservative Blend No 1 in 0.25% gelatine solutions. The initial inoculation level of microbes for this study was $10^4$ to $10^{10}$ cfu/ml. From the Table V it can be seen that both Gram negative and Gram negative bacteria were killed in less than 10 minutes. This also includes Pseudomonas that is dreaded as the nemesis of personal care and pharmaceutical industry. It is important to see that Bacillus subtilis, tough Gram positive bacteria to destroy due to its endosperm protection, was killed within minutes. Similarly, Aspergillus niger, the spores of which are tough to kill but 1% concentration of this blend proved to be lethal for the organism and was destroyed within a hour, notwithstanding its high initial population. Almost, identical results were obtained for the 'Time Kill Study' of Preservative Blend No 2. Thus, the blends of the present invention are very effective against both bacteria and fungi. It is also pertinent to mention here that the various combinations of two component system that were evaluated showed much less efficacy and did not cover the broad antimicrobial activity. This again proved that the combinations of three components, [A], [B] and [C] are required in a definite ratio by weight to deliver a good synergistic performance.

TABLE V (Time Kill Study of Preservative Blend No 1)

| | Time | | | | | | | |
|---|---|---|---|---|---|---|---|---|
| Organism | 0 min | 2 min | 5 min | 10 min | 30 min | 60 min | 120 min | 24 hrs |
| Escherichia coli ATCC 10142 | $3 \times 10^{10}$ | $52.31 \times 10^4$ | $36.23 \times 10^5$ | $469 \times 10^5$ | <10 | <10 | <10 | <10 |
| Staphylococcus aureus ATCC 6538S | $2.2 \times 10^8$ | <10 | <10 | <10 | <10 | <10 | <10 | <10 |
| Bacillus subtilis ATCC 9372 | $15.35 \times 10^2$ | <10 | <10 | <10 | <10 | <10 | <10 | <10 |
| Pseudomonas aeruginosa Immuno type IV | $22.73 \times 10^3$ | <10 | <10 | <10 | <10 | <10 | <10 | <10 |
| Malassezia furfur MTCC 1374 | $49.99 \times 10^4$ | $3.25 \times 10^2$ | 10 | <10 | <10 | <10 | <10 | <10 |

TABLE V-continued (Time Kill Study of Preservative Blend No 1)

| Organism | Time | | | | | | | |
|---|---|---|---|---|---|---|---|---|
| | 0 min | 2 min | 5 min | 10 min | 30 min | 60 min | 120 min | 24 hrs |
| *Aspergillus niger* ATCC 16404 | $2.50 \times 10^7$ | $9.6 \times 10^4$ | $9.96 \times 10^4$ | $6.2 \times 10^4$ | $2.65 \times 10^3$ | <10 | <10 | <10 |
| *Candida albicans* ATCC 10231 | $6.5 \times 10^4$ | $3 \times 10^4$ | <10 | <10 | <10 | <10 | <10 | <10 |

The efficacy of these 'three component' blends was ascertained by performing the challenge tests on the various types of topical personal care formulations viz, a sunscreen cream formulation with SPF 15, W/O cold cream, a face wash, a shampoo formulation, shaving gel and a protein solution that were preserved with 0.4 to 1.0% of the Preservative Blend No 1 and No 2 as exemplified below in the experimental section. Protein hydrolyzate solution was selected since the hydrolyzed proteins (20%) and water form the most supporting environment for the microbes to grow. The protein solution was preserved with 1.0% of Preservative Blend No 1 and challenge tested. The challenge tests were performed according CTFA guideline (Evaluation of preservatives to protect cosmetics' by D. Orth in *Cosmetics and Toiletries* March 91). All formulations containing 0.4 to 1.0% of preservative Blend No 1 or No 2 were challenge tested with initial inoculation level of $10^8$ to $10^{10}$ cfu/ml. In all formulations bacterial as well as yeast count got reduced to >99% within 48 hrs whereas >99% reduction in mould count was observed within 7 days. As per CTFA guideline the 'challenge tests' were continued for 28 days and all formulations, preserved with Blend No 1 or Blend No 2, were found to be quite robust against microbial contamination as shown in Table VI and Table VII.

TABLE VI

Challenge Test performed on Sunscreen Cream formulation preserved with 1.0% Preservative Blend No 1

| TVC (cfu/gm) | *Staphylococcus aureus* ATCC 6538S | *Escherichia coli* ATCC 10142 | *Pseudomonas aeruginosa* Immuno type IV | *Bacillus subtilis* ATCC 9372 | *Candida albicans* ATCC 10231 | *Aspergillus niger* ATCC 16404 |
|---|---|---|---|---|---|---|
| 0 hr | $35.35 \times 10^5$ | $3 \times 10^9$ | $3 \times 10^9$ | $3 \times 10^9$ | $1.05 \times 10^6$ | $11.05 \times 10^6$ |
| 24 hr | $3.33 \times 10^5$ | <10 | <10 | $14.61 \times 10^4$ | $0.8 \times 10^2$ | $6 \times 10^5$ |
| 48 hr | $10.9 \times 10^3$ | <10 | <10 | $28 \times 10^3$ | <10 | $14.9 \times 10^5$ |
| 7 days | <10 | <10 | <10 | <10 | <10 | <10 |
| 14 days | <10 | <10 | <10 | <10 | <10 | <10 |
| 21 days | <10 | <10 | <10 | <10 | <10 | <10 |
| 28 days | <10 | <10 | <10 | <10 | <10 | <10 |

TABLE VII

Challenge Test performed on 20% aqueous protein hydrolyzate preserved with 1.0% Preservative Blend No 1

| TVC (cfu/gm) | *Staphylococcus aureus* ATCC 6538S | *Escherichia coli* ATCC 10142 | *Pseudomonas aeruginosa* Immuno type IV | *Bacillus subtilis* ATCC 9372 | *Candida albicans* ATCC 10231 | *Aspergillus niger* ATCC 16404 |
|---|---|---|---|---|---|---|
| 0 hr | $3.50 \times 10^6$ | $3 \times 10^9$ | $3 \times 10^9$ | $3 \times 10^9$ | $1.05 \times 10^6$ | $11.05 \times 10^6$ |
| 24 hr | $2 \times 10^2$ | <10 | <10 | $14.61 \times 10^4$ | $0.8 \times 10^2$ | <10 |
| 48 hr | <10 | <10 | <10 | $1.8 \times 10^3$ | <10 | <10 |
| 7 days | <10 | <10 | <10 | <10 | <10 | <10 |
| 14 days | <10 | <10 | <10 | <10 | <10 | <10 |
| 21 days | <10 | <10 | <10 | <10 | <10 | <10 |
| 28 days | <10 | <10 | <10 | <10 | <10 | <10 |

Any one with the reasonable level of knowledge of the art would understand that these 'three component' preservative systems can be used with additional anti-microbial compounds or adjuvants that can enhance or boost antimicrobial activity synergistically. The examples of such adjuvants are caprylyl glycol, 1,3-propane diol or EDTA etc.

Example 4

Preparation of Personal Care Formulations

A shampoo, a sunscreen cream, a w/o cold cream, a shaving gel and a face wash were prepared according to the following procedures and preserved with 0.4 to 1.0% levels of the Preservative Blend No 1. The formulations were then tested for the stability and subsequently 'challenge tested' according to CTFA guidelines. The challenge test results of some of the formulations are provided in the description of the invention.

| Components | Trade Name | (% W/W) |
|---|---|---|
| Phase A | | |
| Water (Aqua) | D. M. Water | 44.00 |
| Sodium Lauryl Ether Sulfate[1] | Galaxy LES | 25.00 |
| Disodium Laureth Sulfosuccinate[2] | Galaxy ESS | 15.00 |
| Cocamidopropyl Betaine[3] | Galaxy CAPB | 7.00 |
| Ethylene Diamine Tetra Acetic Acid Disodium Salt | EDTA Na$_2$ salt | 0.10 |
| Phase B | | |
| Cocomonoethanolamide[4] | Galaxy 100 | 3.00 |
| Ethylene Glycol Distearate[5] | Galaxy 610 | 2.00 |
| Phase C | | |
| Polyquaternium-7[6] | Galsilk 7 | 3.00 |
| Silk Amino Acids[7] | Amino Silk SF | 0.50 |
| N-Undecylenoyl monoethaol amide, N-Octanoyl glycine and 2-phenoxyethanol | Preservative Blend No 1 of this patent application | 0.40 |
| Citric acid 50% aq. | Citric Acid | q.s to pH 6.0-6.5 |
| Fragrance, Color | | q.s |

Example 4a

Preparation of Shampoo

| Components | Trade Name | (% W/W) |
|---|---|---|
| Phase A | | |
| Water (Aqua) | D. M. Water | 44.00 |
| Sodium Lauryl Ether Sulfate[1] | Galaxy LES | 25.00 |
| Disodium Laureth Sulfosuccinate[2] | Galaxy ESS | 15.00 |
| Cocamidopropyl Betaine[3] | Galaxy CAPB | 7.00 |
| Ethylene Diamine Tetra Acetic Acid Disodium Salt | EDTA Na$_2$ salt | 0.10 |
| Phase B | | |
| Cocomonoethanolamide[4] | Galaxy 100 | 3.00 |
| Ethylene Glycol Distearate[5] | Galaxy 610 | 2.00 |
| Phase C | | |
| Polyquaternium - 7[6] | Galsilk 7 | 3.00 |
| Silk Amino Acids[7] | Amino Silk SF | 0.50 |
| N-Undecylenoyl monoethaol amide, N-Octanoyl glycine and 2-phenoxyethanol | Preservative Blend No 1 of this patent application | 0.40 |
| Citric acid 50% aq. | Citric Acid | q.s to pH 6.0-6.5 |
| Fragrance, Color | | q.s |

SHAMPOO
Galaxy Surfactants Ltd.
[1]Galaxy LES
[2]Galaxy ESS
[3]Galaxy CAPB
[4]Galaxy 100
[5]Galaxy 610
[6]Galsilk 7
Tri-K Industries
[7]Amino Silk SF Procedure:

Heat all the ingredients of phase A to 75° C. under slow stirring. Add phase B and mix until homogenous. Cool down to room temperature and add phase C, stir until uniform. Adjust pH of the final formulation with 50% citric acid. Blend in fragrance and color.

Example 4b

Preparation of a Sunscreen Cream (SPF 15)

| Components | Trade Name | (% W/W) |
|---|---|---|
| Sunscreen Cream (SPF 15) | | |
| Phase A | | |
| Water (Aqua) | D.M.Water | 64.3 |
| N-Undecylenoyl monoethaol amide, N-Octanoyl glycine and 2-phenoxyethanol | Preservative Blend No 1 of this patent application | 1.00 |
| Glycerin | Glycerin | 2.00 |
| Laureth-9[1] | Galaxy-MW259 | 0.50 |
| PEG-7 Glyceryl Cocoate[2] | Galaxy PEG-7 Glyceryl Cocoate | 2.00 |
| Ethylene Diamine Tetra Acetic Acid Disodium Salt | EDTA Na2 salt | 0.05 |
| Phase B | | |
| Butyl Methoxydibenzoylmethane[3] | GalSORB Avobenzone | 3.00 |
| Octocrylene[4] | GalSORB Octocrylene | 3.00 |
| Ethylhexyl methoxycinnamate[5] | GalSORB OMC | 5.00 |
| Paraffinum Liquidum[6] | Mineral oil | 4.00 |
| Stearic Acid[7] | Stearic Acid | 2.00 |
| Glyceryl Stearate[8] | Glyceryl Stearate | 5.00 |
| Cetearyl Alcohol[9] | Cetearyl Alcohol | 3.50 |
| Isopropyl Myristate[10] | Isopropyl Myristate | 5.00 |
| Phase C | | |
| Fragrance, Color | | q.s |

Galaxy Surfactants Ltd.
[1]Galaxy-MW259
[2]Galaxy PEG-7 Glyceryl Cocoate
[3]GalSORB Avobenzone
[4]GalSORB Octocrylene
[5]GalSORB OMC
Apar Industries
[6]Mineral oil
VVF Ltd.
[7]Stearic Acid
[9]Cetostearyl Alcohol
Fine Organics Pvt. Ltd.
[8]Glyceryl Mono stearate
Subash Chemical Ind.
[10]Isopropyl Myristate Procedure: Heat Phase A up to 80° C., and Phase B up to 75° C. with stirring. Add phase B to phase A with constant stirring. Homogenise for 2 minutes, continue stirring for 15 minutes. Cool down to 40° C. and add phase C. Mix well.

Efficacy Testing: In vitro SPF: 17, BSR: +++

Example 4c

Preparation of Face Wash Formulation

| Components | Trade Name | (% W/W) |
|---|---|---|
| Face Wash | | |
| Phase A | | |
| Water (Aqua) | D.M.Water | 57.90 |
| Sodium Cocoyl Glycinate[1] | Galsoft SCG | 10.00 |
| Glycerin | Glycerin | 15.00 |
| Cocamidopropyl Betaine[2] | Galaxy CAPB | 8.00 |
| Ethylene Diamine Tetra Acetic Acid Disodium Salt | EDTA Na$_2$ salt | 0.10 |

| Face Wash | | |
|---|---|---|
| Components | Trade Name | (% W/W) |
| Phase B | | |
| Cetearyl Alcohol[3] | Cetearyl Alcohol | 1.00 |
| Ethylene Glycol Distearate[4] | Glyceryl mono stearate | 3.00 |
| Glyceryl stearate[5] | Galaxy 610 | 2.00 |
| PEG 150 Distearate[6] | Aculyn-60 | 0.50 |
| Cocomonoethanolamide[7] | Galaxy 100 | 2.00 |
| Phase C | | |
| Polyquaternium-7[8] | Galsilk 7 | 2.00 |
| Aqua/Water, Sodium PCA, Wheat Amino Acid, *Symphytum Officinale* (Comfrey) Extract, Panthenol, Hydroxyproline[9] | Fission Skin Moisture | 2.00 |
| N-Undecylenoyl monoethanol amide, N-Octanoyl glycine and 2-phenoxyethanol | Preservative Blend No. 1 | 1.00 |
| Fragrance, Color | | q.s |

Galaxy Surfactants Ltd.
[1]Galsoft SCG
[2]Galaxy CAPB
[4]Galaxy 610
[7]Galaxy 100
[8]Galsilk 7
Tri-K Industries
[9]Fission Skin Moisture
VVF Ltd.
[3]Cetearyl Alcohol
Fine Organics Pvt. Ltd.
[5]Glyceryl Stearate
Rohm & Haas
[6]Aculyn 60

Procedure: Heat all the ingredients of phase A to 75° C. under slow stirring. Add phase B and mix until homogenous. Cool to room temperature and add phase C, stir until uniform. Blend in fragrance and color. Adjust pH of the formulation between 6.5-7.5.

Example 4d

Preparation of a Cold Cream

| W/O Cold Cream | | |
|---|---|---|
| Components | Trade Name | (% W/W) |
| Phase A | | |
| Water (Aqua) | D. M. Water | 42.45 |
| Triethanolamine | Triethanolamine | To Adjust pH neutral |
| PEG-7 Glyceryl Cocoate[1] | Galaxy PEG-7 Glyceryl Cocoate | 2.00 |
| Ethylene Diamine Tetra Acetic Acid Disodium Salt | EDTA Na2 salt | 0.05 |
| Phase B | | |
| Glyceryl Stearate[2] | Glyceryl Stearate | 5.00 |
| Bees Wax | Bees Wax | 3.00 |
| Paraffinum Liquidum[3] | Mineral oil | 35.00 |
| Stearic Acid[4] | Stearic Acid | 1.00 |
| Cetearyl Alcohol[5] | Cetearyl Alcohol | 3.50 |
| DC 245[6] | Cyclomethicone | 5.00 |

| W/O Cold Cream | | |
|---|---|---|
| Components | Trade Name | (% W/W) |
| Phase C | | |
| Polyquaternium-7[7] | Galsilk 7 | 2.00 |
| N-Undecylenoyl monoethaol amide, N-Octanoyl glycine and 2-phenoxyethanol | Preservative Blend No 1 of this patent application | 1.00 |
| Fragrance, Color | | q.s |

Galaxy Surfactants Ltd.
[1]Galaxy PEG-7 Glyceryl Cocoate
[7]Galsilk 7
Fine Organics Pvt. Ltd.
[5]Glyceryl Stearate
Apar Industries
[3]Mineral oil
VVF Ltd.
[4]Stearic Acid
[5]Cetearyl Alcohol
Fine Organics Pvt. Ltd.
[5]Glyceryl Stearate Procedure: Heat Phase A up to 80° C., and Phase B up to 75° C. with stirring. Add phase B to phase A with constant stirring. Homogenise for 2 minutes, continue stirring for 15 minutes. Cool down to 40° C. and add phase C. Mix well.

Example 4e

Preparation of a Shaving Gel

| Shaving Gel | | |
|---|---|---|
| Components | Trade Name | (% W/W) |
| Phase A | | |
| Water (Aqua) | D. M. Water | 57.90 |
| Hydroxy Ethyl Cellulose (HEC)[1] | Natrosol HHX | 1.2 |
| Myristic Acid | Myristic Acid[2] | 5.00 |
| Palmitic Acid | Palmitic Acid[3] | 10.00 |
| Cetostearyl 20 Mole Ethoxylate[2] | | 3.00 |
| PEG 150 Di Stearate[3] | Aculyn 60 | 1.00 |
| Oleyl alcohol 20 mole ethoxylate[4] | Oleth-20 | 2.00 |
| Allaintion | | 0.10 |
| Ethylene Diamine Tetra Acetic Acid Disodium Salt | EDTA Na2 salt | 0.10 |
| Phase B | | |
| Triethanolamine | Triethanolamine | To adjust pH 8.5 |
| Phase C | | |
| Glycerin | Glycerin | 10.00 |
| Polyquaternium-7[5] | Galsilk 7 | 1.50 |
| Sodium Lauroyl Sarcosinate[6] | Galsoft NaLS | 10.00 |
| N-Undecylenoyl monoethaol amide, N-Octanoyl glycine and 2-phenoxyethanol | Preservative Blend No 1 of this patent application | 1.00 |
| Fragrance, Color | | q.s |

Ashland Inc.
[1]Natrosol HHX
Venus Ethoxyethers Pvt. Ltd.
[2]Cetostearyl 20 mole ethoxylate
Rohm & Haas
[3]Aculyn 60
Rohm & Haas
[4]Oleth-20
Galaxy Surfactants Ltd.
[5]Galsoft NaLS
[6]Galsilk 7

Procedure:

Disperse hydroxyethyl cellulose (HEC) in water. Heat swelled HEC up to 75-80° C., add remaining ingredients of phase A and stir. Heat phase A and B separately up to 75-80° C. and mix. Once temperature reaches 75° C.' add phase B to A with continuous but moderate stirring. (soap formation stage). Maintain temperature at 75-80° C. for 45 minutes and stir. (saponification stage). Finally add phase C and Phase D once temperature reaches 35° C. Add Preservative Blend No. 1, fragrance and colour.

The invention claimed is:

1. An antimicrobial preservative composition for preservation of topical personal care formulations consisting of:
an undecylenic acid derivative depicted by Formula (I), wherein, M=—NH—CH$_2$CH$_2$—OH;

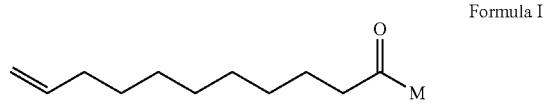

Formula I

[B] one or more octanoic acid derivatives depicted by Formula (II), wherein, M=—NH—CH$_2$CH$_2$—OH or —NH—CH$_2$COOH;

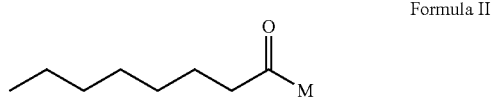

Formula II and [C] 2-phenoxy ethanol;
wherein, each of the two components [A] and [B] is present in the range of 5 to 20% by weight and together [A] and [B] constitute 10 to 30% by weight and
the 2-phenoxy ethanol, component [C], is present in the range of 70 to 90% by weight of the total preservative composition.

2. The antimicrobial preservative composition as claimed in claim 1, wherein the antimicrobial preservative composition consists of a mixture of
[A] N-undecylenoyl monoethanol amide,
[B] N-octanoyl monoethanol amide and
[C] 2-phenoxy ethanol
and wherein, [A] and [B] together constitute 20% by weight of the preservative composition and [C] is 80% by weight of the preservative composition.

3. The antimicrobial preservative composition as claimed in claim 1, wherein the antimicrobial preservative composition consists of a mixture of
[A] N-undecylenoyl monoethanol amide,
[B] N-octanoyl glycine and
[C] 2-phenoxy ethanol
wherein, [A] is present in 20% by weight and [B] is present in 10% by weight of the preservative composition and [C] is 70% by weight of the preservative composition.

4. The antimicrobial preservative composition as claimed in claim 1, wherein the antimicrobial preservative composition consists of a mixture of
[A] N-undecylenoyl monoethanol amide,
[B] N-capryloyl glycine and
[C] 2-phenoxy ethanol
wherein, [A] and [B] together constitute 30% by weight of the preservative composition and [C] is 70% by weight of the preservative composition.

5. The antimicrobial preservative composition as claimed in claim 1, wherein, the antimicrobial preservative composition consists of a mixture of
[A] N-undecylenoyl monoethanol amide,
[B] N-octanoyl glycine and
[C] 2-phenoxy ethanol
wherein [A] is 10% by weight, [B] is 7.5% by weight and [C] is 82.5% by weight of the preservative composition.

6. A method for preserving a personal care product containing an aqueous phase from microbial attack comprising adding to the personal care product the antimicrobial preservative composition of claim 1 from about 0.5 to 2.5% by weight of the total personal care product.

7. A personal care formulation for topical application comprising the antimicrobial preservative composition as claimed in claim 1.

8. The personal care formulation as claimed in claim 7, wherein the personal care formulation is selected from lotions, creams, solutions, body-washes, shampoos, serums, wipes and emulsions.

9. The personal care formulation as claimed in claim 7, further comprising personal care ingredients selected from the group consisting of solvents, surfactants, emulsifiers, rheology modifiers, conditioners, emollients, skin caring ingredients, preservatives, thickeners, lubricants, fillers, antioxidants, active ingredients, dermatologically active ingredients, fragrances and mixtures thereof.

* * * * *

UNITED STATES PATENT AND TRADEMARK OFFICE
CERTIFICATE OF CORRECTION

PATENT NO. : 9,661,847 B2
APPLICATION NO. : 14/357663
DATED : May 30, 2017
INVENTOR(S) : Nirmal Koshti et al.

It is certified that error appears in the above-identified patent and that said Letters Patent is hereby corrected as shown below:

In the Claims

Column 25, Line 14, Claim 1, before "an" insert -- [A] --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*